(12) United States Patent
Sheridan

(10) Patent No.: US 9,897,534 B2
(45) Date of Patent: Feb. 20, 2018

(54) METHOD AND APPARATUS TO DETERMINE COLOUR OF EGG YOLK

(71) Applicant: Nix Sensor Ltd., Hamilton (CA)

(72) Inventor: Matthew Sheridan, Burlington (CA)

( * ) Notice: Subject to any disclaimer, the term of this patent is extended or adjusted under 35 U.S.C. 154(b) by 0 days.

(21) Appl. No.: 15/292,414

(22) Filed: Oct. 13, 2016

(65) Prior Publication Data
US 2017/0115209 A1  Apr. 27, 2017

Related U.S. Application Data

(60) Provisional application No. 62/245,541, filed on Oct. 23, 2015.

(51) Int. Cl.
| | |
|---|---|
| *G01J 3/46* | (2006.01) |
| *G01N 21/25* | (2006.01) |
| *G01N 21/01* | (2006.01) |
| *G01N 33/08* | (2006.01) |
| *G01J 3/50* | (2006.01) |
| *G01N 21/03* | (2006.01) |
| *G01N 21/47* | (2006.01) |

(52) U.S. Cl.
CPC .............. *G01N 21/251* (2013.01); *G01J 3/50* (2013.01); *G01J 3/501* (2013.01); *G01N 21/01* (2013.01); *G01N 21/03* (2013.01); *G01N 21/255* (2013.01); *G01N 33/08* (2013.01); *G01N 2021/4757* (2013.01); *G01N 2021/4769* (2013.01); *G01N 2201/0221* (2013.01); *G01N 2201/062* (2013.01); *G01N 2201/064* (2013.01); *G01N 2201/08* (2013.01)

(58) Field of Classification Search
CPC ........ G01J 3/02; G01J 3/46; G01J 3/50; G01J 3/51; G01J 3/52; G01N 21/01; G01N 21/02; G01N 21/25; G01N 33/08
See application file for complete search history.

(56) References Cited

U.S. PATENT DOCUMENTS

2010/0112183 A1* 5/2010 Gurner ................... A47J 43/10
426/614

\* cited by examiner

*Primary Examiner* — Abdullahi Nur
(74) *Attorney, Agent, or Firm* — Ridout & Maybee LLP; Mark A. Koch

(57) ABSTRACT

The present concept is a method of preparing an egg to determine the color of the egg using an egg yolk cover. The egg yolk cover is dome-shaped with a base edge and inspection area. The egg yolk cover eliminates ambient light from impinging on the egg yolk and is used in combination with a light sensor to determine the color of egg yolks. The light sensor includes a single flat printed circuit board with a top and bottom side which includes at least one LED light and one color sensor, at least one light pipe receiving light from the LED and transmitting it onto a substrate at an angle theta and a tube frame including an optical tube for receiving light reflections from the substrate. The light pipes and the tube frame are compression fit between the printed circuit board and a lower housing. To determine the color of the egg yolk, the egg is first cracked onto a flat surface. The egg yolk cover is then placed over the egg yolk and the color sensor is placed onto the inspection area to measure the color.

19 Claims, 9 Drawing Sheets

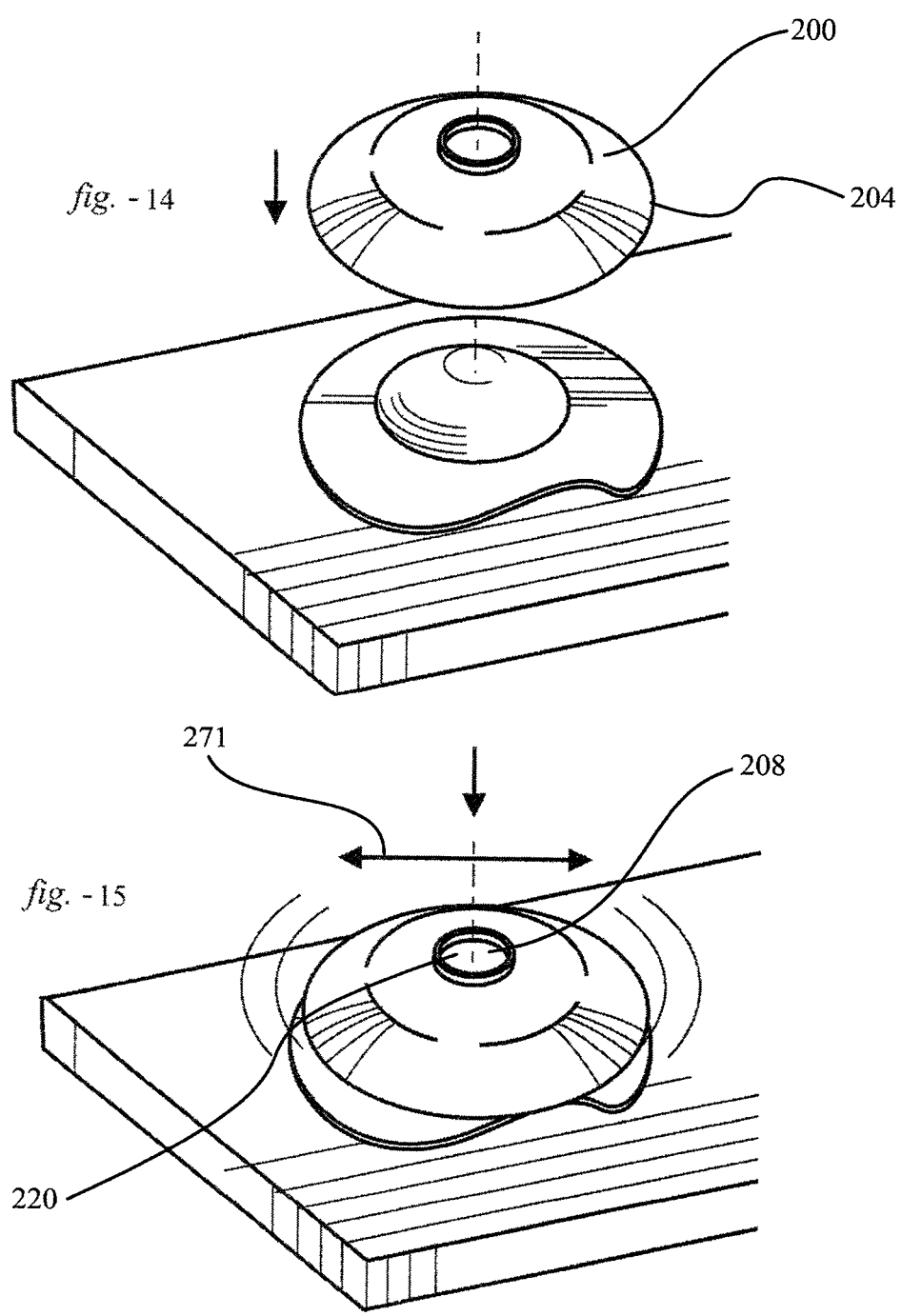

METHOD AND APPARATUS TO DETERMINE COLOUR OF EGG YOLK

This application claims priority from the previously filed provisional application No. 62/245,541, filed on Oct. 23, 2015 by Nix Sensor Ltd. under the title: METHOD AND APPARATUS TO DETERMINE COLOUR OF EGG YOLK.

FIELD OF THE INVENTION

The present concept relates to a device for measuring and analysing colours and more particularly it relates to a small handheld inexpensive colour measuring device which can interface via Bluetooth with smartphones and convert the colour readings into any number of current colour models, or spaces.

BACKGROUND OF THE INVENTION

There is a need to quickly and accurately be able to measure colours on a variety of different surfaces and convert the colour measurement into a number of standard colour spaces.

There are a number of prior art devices which have attempted to measure colour each with shortcomings normally related to accuracy reproducibility, portability, cost of manufacture and inability to convert readings into a number of standard colour spaces used by different industries.

Studies have shown that there exist a cultural preference in the colour of the food people consume, therefor in the egg industry the colour of the yolk is closely controlled and a vital step in the control process is accurately measuring the yolk colour. There is a need for a quick, accurate and cost effective way of measuring the colour of the egg yolk.

A number of prior art devices exist in the industry that can be utilized to measure the colour of the yolk. Two such methods are the DSM Egg yolk colour fan and the egg quality measurement device. Though both methods can provide the measurements but they are not without their limitations and shortcomings. The egg yolk colour fan is fast and inexpensive, given it is a qualitative method of comparing coloured swatches to the yolk via the naked eye, it's accuracy and precision is a function of the end user. The second method mentioned is the egg quality measuring device, which utilizes a colour sensor and a light source. The light illuminates the yolk at prescribed angle and the reflected light is diffused into the sensor. This method is more accurate and precise since it is quantitative, but the size, complexity and cost of the apparatus make it less appealing to the end users.

SUMMARY

The present concept is an egg yolk cover for housing the liquid portion of an egg between the cover and a flat surface for the purpose of measuring egg yolk color. The egg yolk cover comprises:
  a) an opaque cover adapted to cover the liquid portion of an egg, the cover includes a base edge which contacts with the flat surface and adapted to create a substantially light tight seal with the flat surface;
  b) wherein the cover includes a transparent inspection area adapted for viewing the egg yolk.

Preferably wherein the cover is dome shaped and includes a flattened crown portion which is substantially parallel to the flat surface.

Preferably wherein the inspection area is an aperture in the flattened crown portion.

Preferably wherein the aperture includes a transparent window within the aperture which impinges onto the egg yolk.

Preferably wherein the cover defines a yolk depth wherein the flattened crown portion is dimensioned to be at a preselected height above the flat surface and selected to fall in the range from 6 to 12 mm inclusively.

Preferably wherein the cover defines a preselected volume between the cover and flat surface which is sufficient to house the egg yolk.

Preferably wherein the preselected volume is selected to fall in the range from 20 ml to 40 ml inclusively.

The present concept is also a method of determining the color of an egg yolk. The method comprises the following steps:
  a) cracking an egg onto a flat surface such that a liquid portion rests on the flat surface;
  b) placing a cover over the egg yolk the cover includes;
    i. an opaque cover adapted to cover the liquid portion of an egg, the cover includes with a base edge which contacts with the flat surface and adapted to create a substantially light tight seal with the flat surface;
    ii. wherein the cover includes a transparent inspection area adapted for viewing the egg yolk;
  c) deploying a color sensor onto the inspection area to measure the yolk color.

Preferably wherein the cover is dome shaped and includes a flattened crown portion which is substantially parallel to the flat surface.

Preferably wherein the inspection area is an aperture in the flattened crown portion.

Preferably wherein the aperture includes a transparent window within the aperture which impinges onto the egg yolk.

Preferably wherein the cover defines a yolk depth wherein the flattened crown portion is dimensioned to be at a preselected height above the flat surface and selected to fall in the range from 6 to 12 mm inclusively.

Preferably wherein the cover defines a preselected volume between the cover and flat surface which is sufficient to house the egg yolk.

Preferably wherein the preselected volume is selected to fall in the range from 20 ml to 40 ml inclusively.

Preferably wherein the light sensor is a portable colour sensor for measuring colour of a substrate comprising:
  a) a single flat printed circuit board with a top & bottom side which includes at least one LED light and one colour sensor;
  b) at least one light pipe receiving light from the LED and transmitting it onto a substrate at an angle theta;
  c) a tube frame including an optical tube for receiving light reflections from the substrate; and
  d) wherein the light pipes and the tube frame, are compression fit between the printed circuit board and a lower housing.

Preferably wherein the LED light is directed perpendicularly away from the printed circuit board and wherein the light pipe is an arcuate member bending the light to achieve the angle theta.

Preferably wherein the light pipe abutting at one end to the LED and connecting at the other end at a light emitting port in the lower housing.

Preferably wherein the light emitting port is located within a light cavity which is an inverted dome with the bottom terminating at a contact surface.

Preferably wherein the flattened crown portion contacting with the contact surface of the lower housing of the lower housing of the colour sensor.

BRIEF DESCRIPTION OF THE DRAWINGS

The present concept will be described by way of example only with reference to the following drawings in which:

FIG. 14 depicts the procedure for deploying the dome shaped cover over the yolk.

FIG. 15 depicts moving the cover for ensuring an unobstructed view and full contact between the yolk and the transparent window within the aperture.

DETAILED DESCRIPTION OF THE PREFERRED EMBODIMENTS

Components of the present concept the portable colour sensor 100 are depicted in the attached figures and shown in various stages of assembly and completion for the benefit of the reader.

Figure 1:
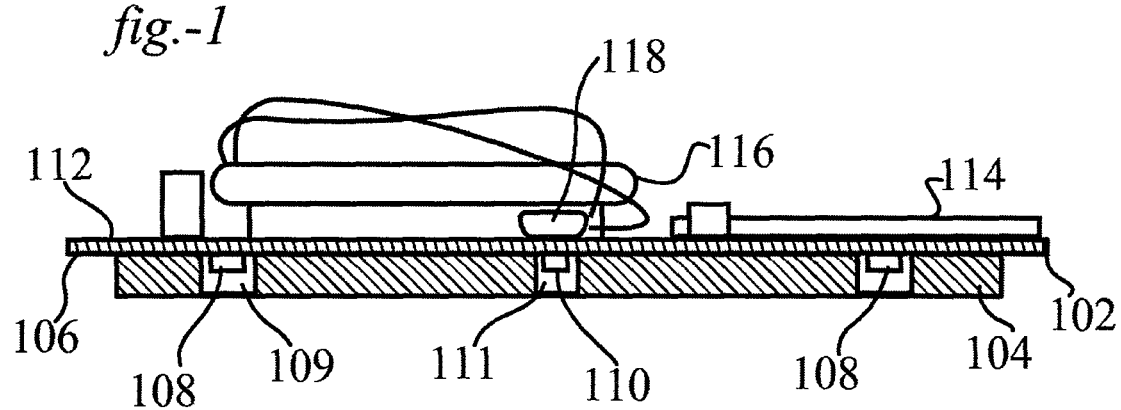
FIG. 1 is a partial side cross sectional view of the printed circuit board used in the present concept together with the gasket mounted on the bottom side and electrical components on the top side.

FIG. 1 for example shows the single printed circuit board PCB 102 used in the present concept together with a gasket 104 mounted on a bottom side 106 having openings 109 for LEDS 108 and opening 111 for colour sensor 110. Colour sensor 110 is a true colour sensor rather than an RGB sensor.

PCB 102 includes a top side 112 at least one integrated circuit 114 a battery 116 and a hard wired interface namely a micro USB port 118 for calibration and data exchange purposes.

Figure 2:
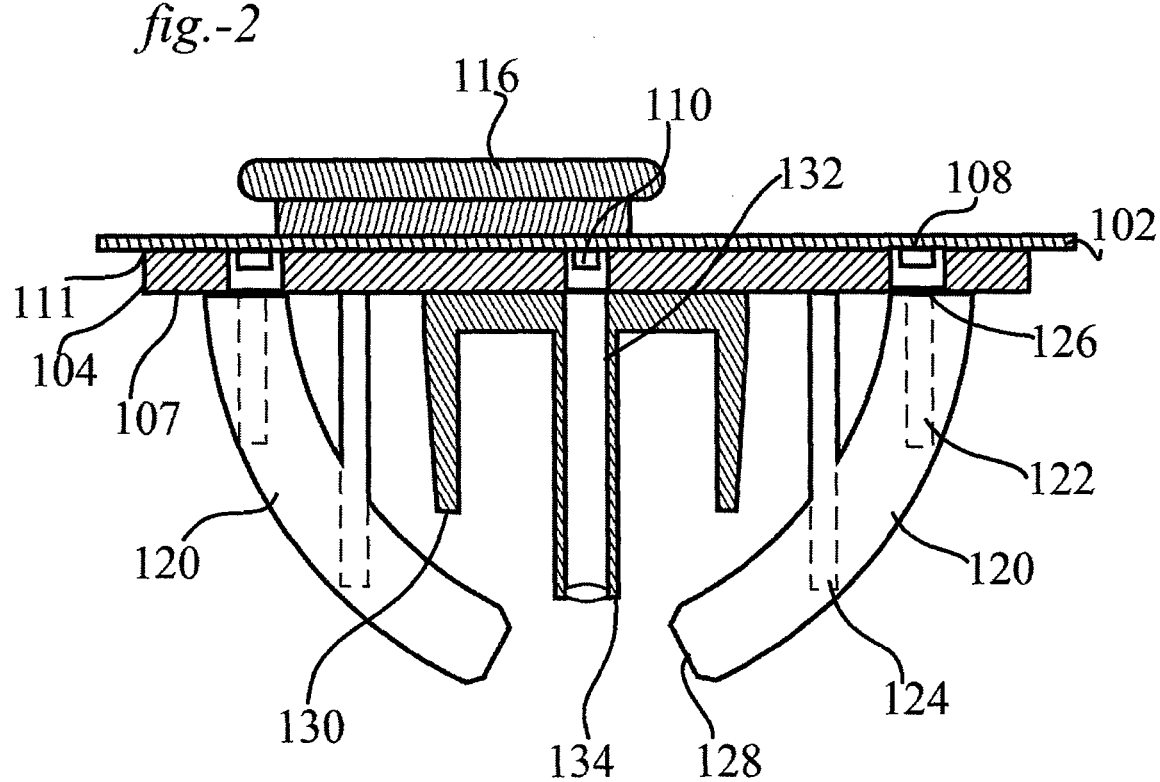
FIG. 2 is a schematic partial cross sectional view of the printed circuit board shown together with an optical tube and light pipes mounted onto a sealing surface of a gasket.

FIG. 2 shows the orientation of various additional components relative to the print circuit board 102 namely left and right light pipes 120 each also having a first flange 122 and a second flange 124, a receiving end 126 and a transmitting end 128. Receiving end 126 abuts against gasket 104 in order that light from LEDS 108 can be transmitted down through light pipe 120 and out through transmitting end 128.

Further there is a tube frame 130 which includes an optical tube 132 having a tube end 134 also abutting and mounted onto gasket 104 for receiving light through optical tube 132 and transmitting the received light onto colour sensor 110.

The components are not assembled in the condition shown in FIG. 2 but rather only the orientation of these components relative to the print circuit board in shown in FIG. 2.

Figure 3:
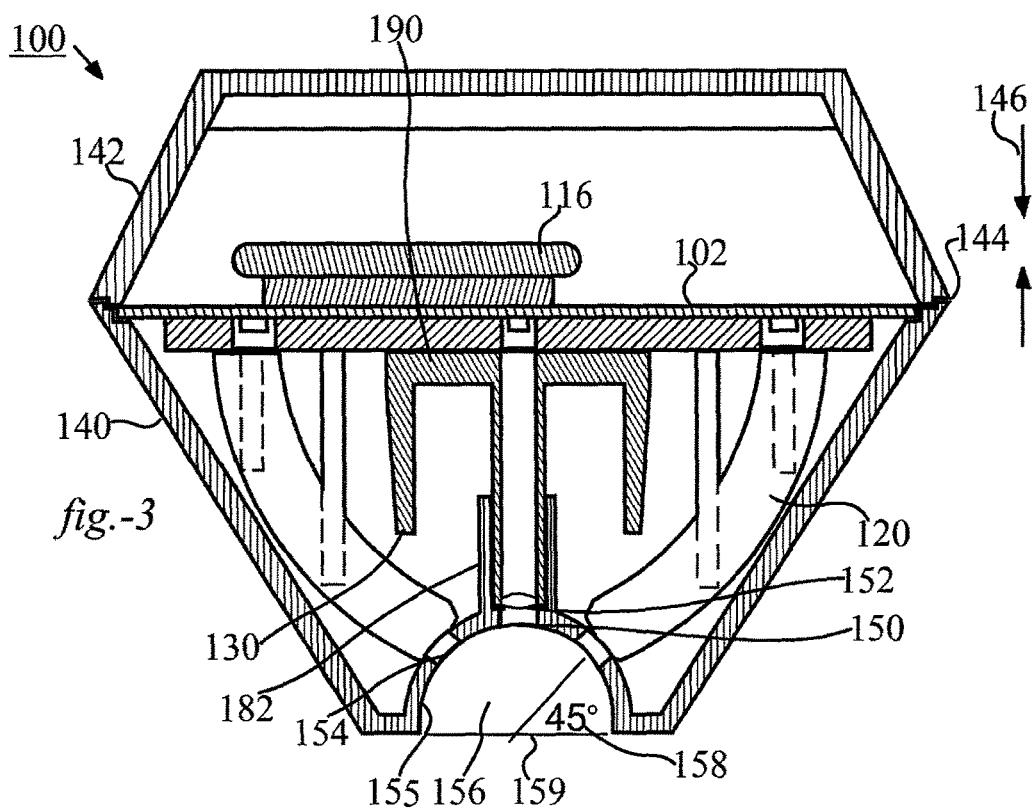
FIG. 3 is a schematic cross sectional view of the print circuit board together with light pipes and a tube frame mounted in a lower housing and an upper housing.

FIG. 3 shows the assembly of the printed circuit board 102 together with the light pipes 120 and the tube frame 130 all mounted into lower housing 140 and capped off with an upper housing 142 at a joint 144. All of the internal components are compression fit show by arrows 146 wherein the PCB 102 is urged downwardly into lower housing 140 thereby pushing downwardly upon the light pipes 120 and tube frame 130, in effect creating a sandwich effect wherein the light pipes 120, tube frame 130 and dust cover 152 are held in place.

Lower housing 140 also includes a lens dust cover 152, a receiving port 150 and defines a contact surface 148. Lower housing 140 also includes light emitting ports 154 and a light cavity 156. Light enters through light emitting ports 154 at an angle theta 158.

Figure 4:
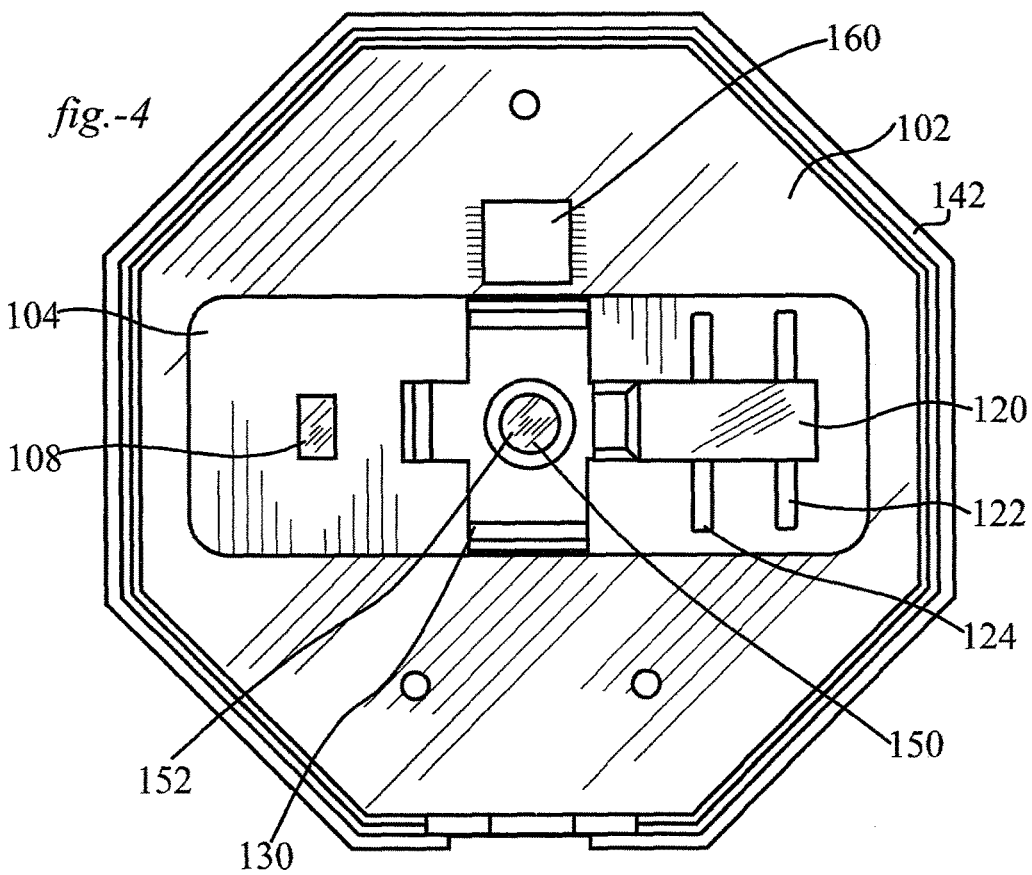
FIG. 4 is a top schematic plan view of the print circuit board mounted into the lower housing.

FIG. 4 is a schematic plan view of the bottom side 106 of printed circuit board 102 with one light pipe 120 shown in position wherein on the other side the LED 108 is clearly visible through opening 109 in gasket 104. Also shown in position is tube frame 130 and dust cover lens 152 at the bottom of receiving port 150. Additionally the first and second flanges 122 and 124 of light pipe 120 are also visible together with the joint 144 of the upper housing 142.

Figure 5:
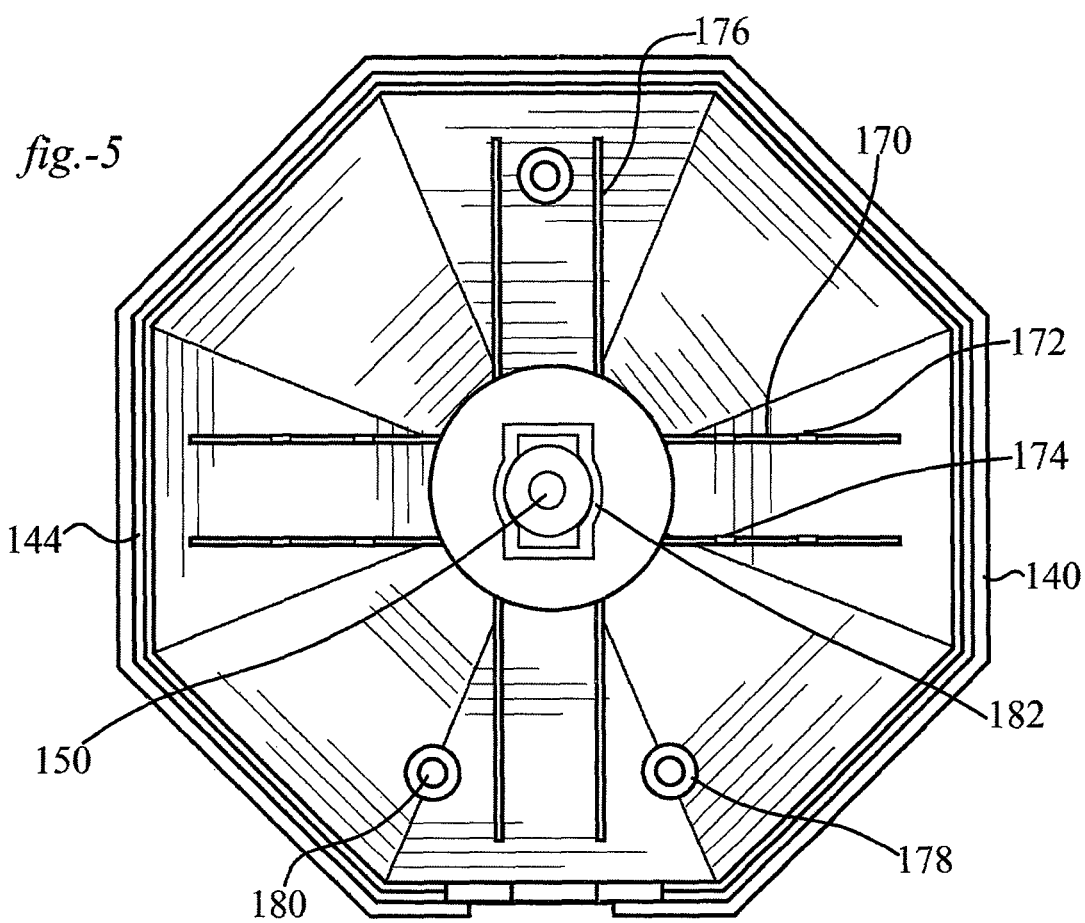
FIG. 5 is a top plan view of the lower housing prior to the installation of the light pipes and tube frame and printed circuit board.
Figure 6:
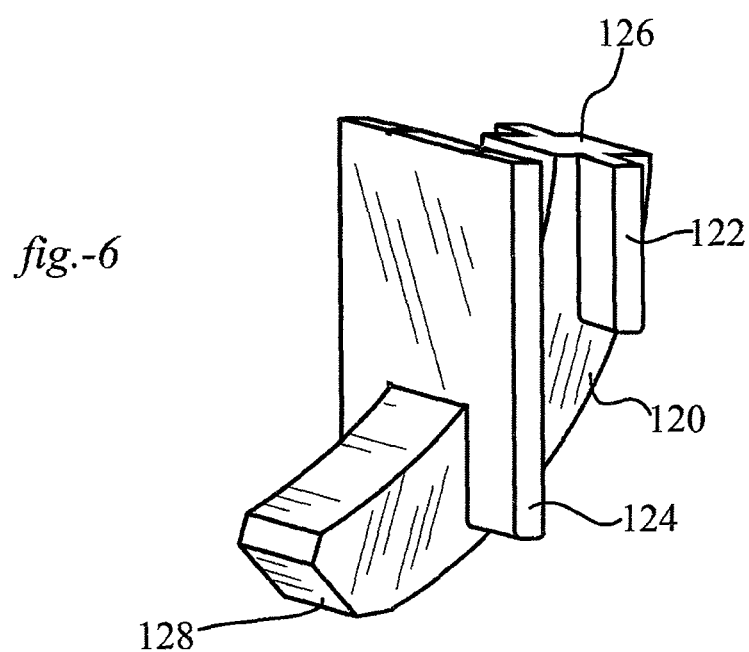
FIG. 6 is schematic perspective view of the light pipe.

FIG. 5 is a plan view looking into the cavity of lower housing 140 with all of the components removed showing a set of four light pipe ribs 170 each having a first slot 172 and a second slot 174 that register and slideably engage with first flange 122 and second flange 124 respectively of light pipe 120.

There are four additional support ribs 176 upon which the printed circuit board 102 rests and three abutments 178 each with a screw hole 180 for fastening print circuit board onto lower housing 140.

The reader will see that the first flange 122 slideably engages with first slot 172 and second flange 124 of light pipe 120 slideably engages with second slot 174. In this manner light pipes 120 are slideably urged into position into the lower housing 140. Additionally dust cover lens 152 is placed into the bottom of tube receiver 182 and optical tube 132 is slideably received within tube receiver 182 thereby placing tube frame 130 in place into lower housing 140.

Thereafter PCB 108 is adhered to with gasket 104 at contact surface 111 is further placed with sealing surface 107 on top of the light pipes and the tube frame 130 thereby compressing gasket 104 which is made of a resiliently biased material in order to create a seal around the base 190 of tube frame 130 and also a seal around the receiving end 126 of light pipe 120 thereby ensuring that light which is conducted down light pipe 120 is not inadvertently transmitted into optical tube 132 directly from LED 108 or indirectly from light pipes 120. Contact surface 111 and sealing surface 107 preferably have pressure sensitive adhesive thereon.

Figure 7:
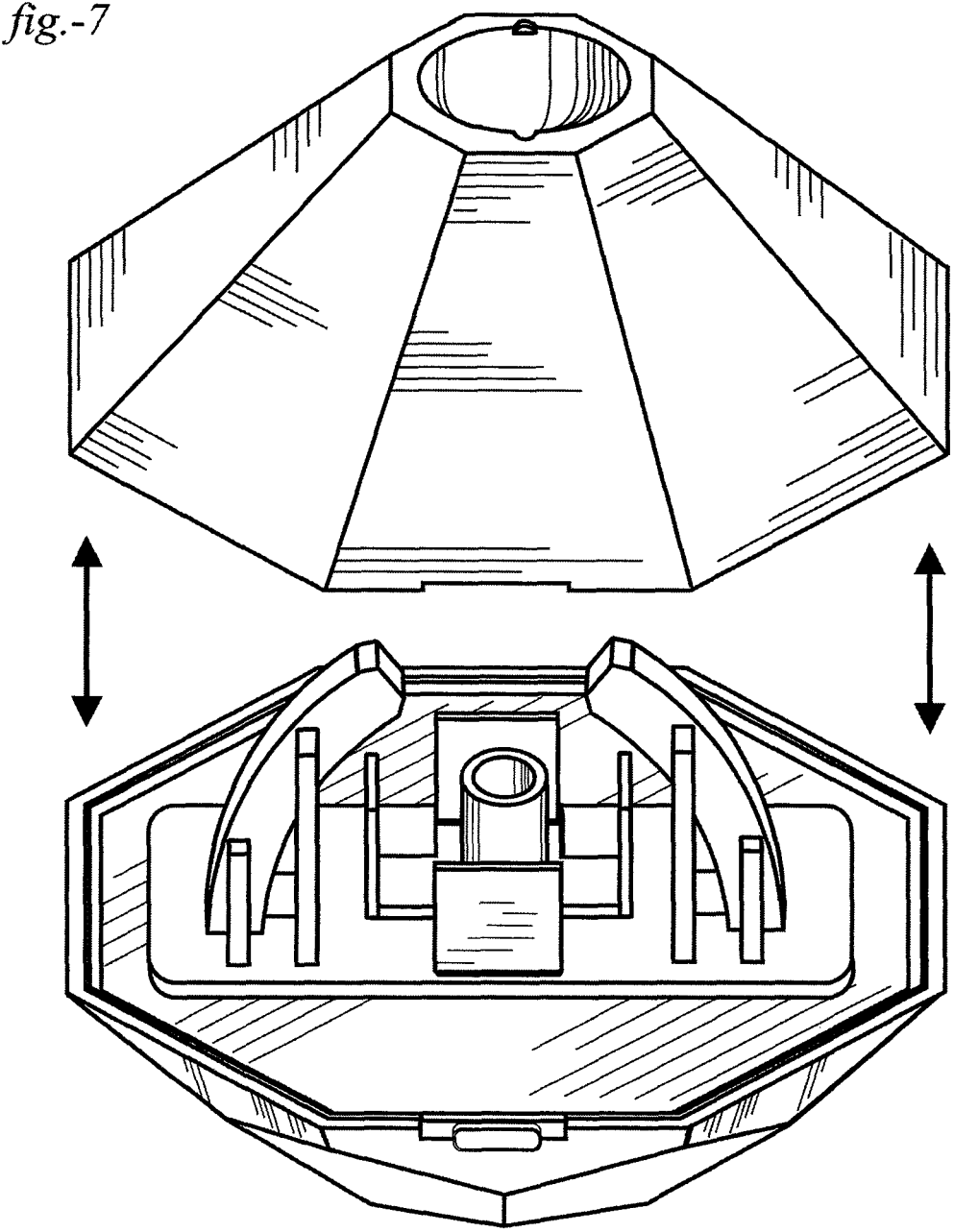
FIG. 7 is an inverted schematic exploded view of the printed circuit board together with the tube frame, light pipes, and the lower and upper housings.

FIG. 7 schematically shows the orientation of lower housing 140 relative to the upper housing 142 and the print circuit board 102 and the light pipes 120 and the tube frame 130.

FIG. 3 shows the angular relationship theta 158 of the light relative to the contact surface 148. This geometrical layout is often referred to as a 45/0 geometry in which illumination of the sample is accomplished at an angle of 45° and the colour sensor 110 receives a portion of the light reflected from the sample at an angle of approximately 0° plus or minus 8°. This geometry is used in order to minimize specular reflections and allow only few reflections to be transmitted through the optical tube 132.

In order to reduce manufacturing costs, time and componentry light pipes 120 have been configured such that a single flat print circuit board PCB 102 can be utilized to mount all of the electrical and electronic componentry.

The LEDS used have a broad parallel spectrum of visible light such that all wavelengths of visible light are emitted by the LEDS 108. In order to ensure consistency and reproducibility components having extremely low drift and low temperature coefficient variances are utilized throughout the device.

Readings obtained from the colour sensor are fed through on board integrated circuitry processing units which provide a predictable, stable and reproducible output.

The unit includes an integral Bluetooth transmission device for wirelessly transmitting data to a smartphone which together with a smartphone application for presenting the data in usable format.

It is also possible to communicate through a hardwired mini USB port 118 to a laptop or other computer. The device is calibrated through the hardwired mini USB port 118 prior to the shipping.

The outputs are converted into usable colour spaces including the well known RGB colour space, HSL colour space, HSV colour space, LAB colour space, XYZ colour space and is also converted into HTML, CMYK or Pantone® units. The processor software application is able to convert to any print system using a delta e calculation to determine what available paint is closest (mathematically) to the scanned sample.

The contact surface 148 is placed against a substrate or surface 159 to be analysed for colour such as a painted wall, skin, and a host of other surfaces and materials.

Light emitted from is conducted down light pipes 120 and exits into light cavity 15 at an angle theta 158 onto a substrate 159 to be measured. Some of the light is reflected back up optical tube 132 where it is received by color sensor 110 and a measurement is taken and recorded.

Components of the present concept the yolk colour sensor are depicted in the attached figures and shown in various stages of assembly and illustrates the method and apparatus for the benefit of the reader.

Figure 8:
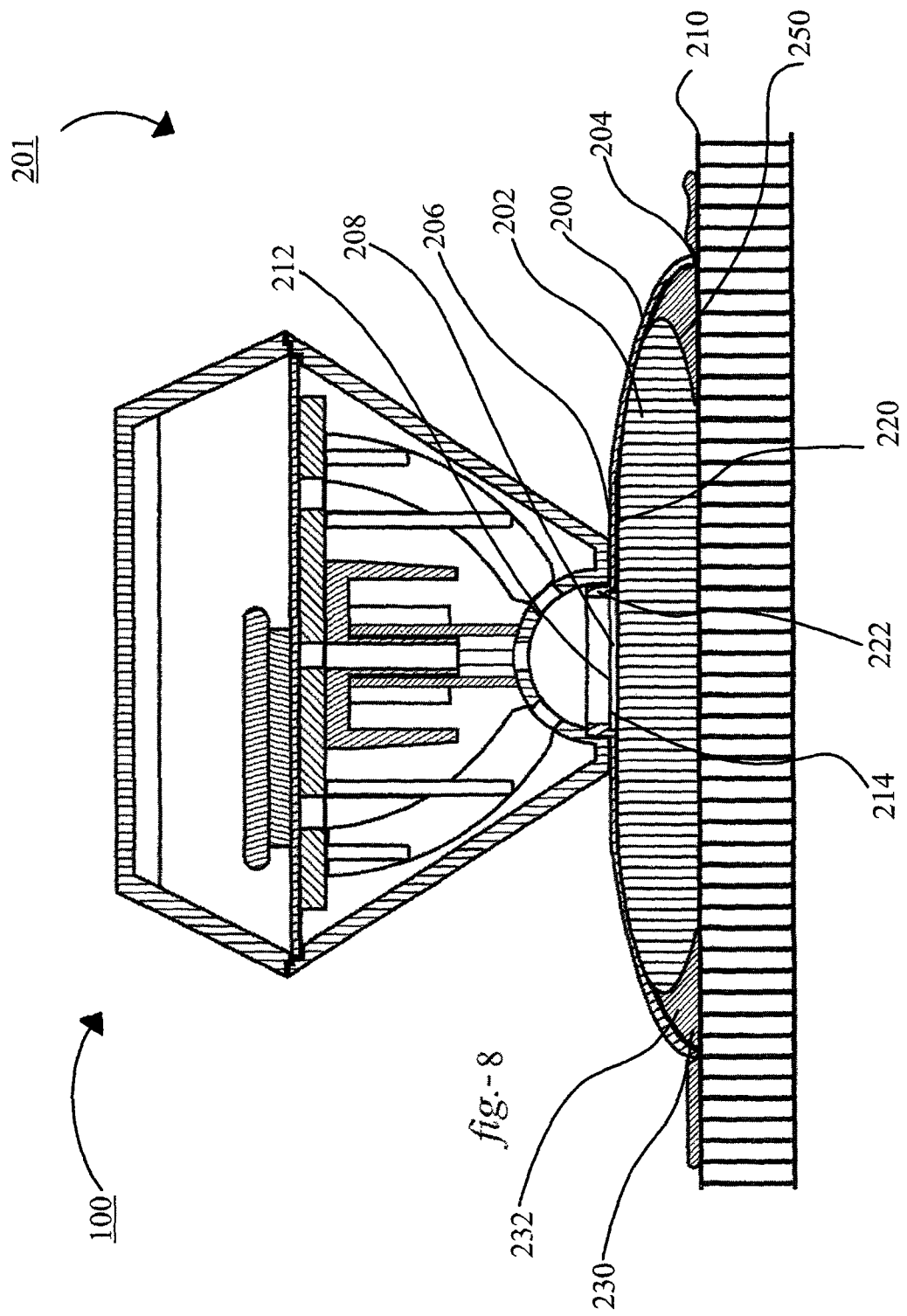
FIG. 8 is a schematic cross sectional view of the colour sensor in FIG. 3 mounted on a dome shaped cover, deployed onto an entire egg yolk in its cavity on top of an opaque flat surface.
Figure 9:
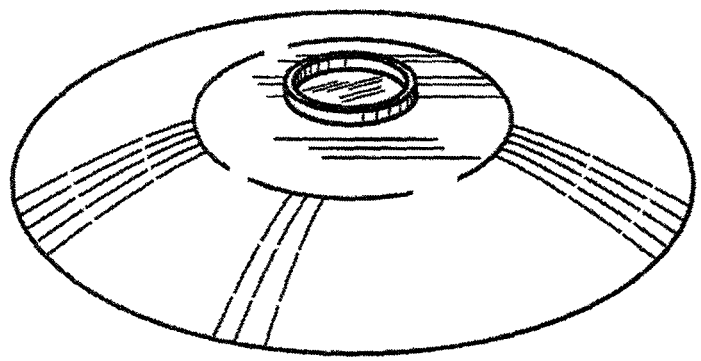
FIG. 9 is an perspective view of the top of the dome shaped cover.

FIG. 8 shows a cross sectional view of the dome shaped cover 200 deployed with a colour sensor 100 that will house an egg yolk 202 over a substantially horizontal flat surface 210. The base edge 204 makes contact with the horizontal flat surface 210 providing a circumferential light tight seal, thus minimizing the intrusion of the outside light.

There exists a flattened crown portion 206 that is substantially parallel in relation to the horizontal flat surface 210. This feature ensures that the yolk top surface 220 is parallel in relation to the transparent window 208, which is critical in producing the desired reflection and refraction angles. Transparent window 208 as depicted is preferably round however could also be a multitude of other shapes including but not limited to: square, triangular or a polygon. Transparent window 208 is preferably made of transparent plastic having known optic properties, but may also be made of other materials such as, including but not limited to, glass with known optic properties.

Situated at the centre of the flattened crown portion is the transparent inspection area 212 containing an aperture 214 with a transparent window 208 onto which the yolk top surface 220 impinges, continuously making contact with transparent window 208.

Figure 10:
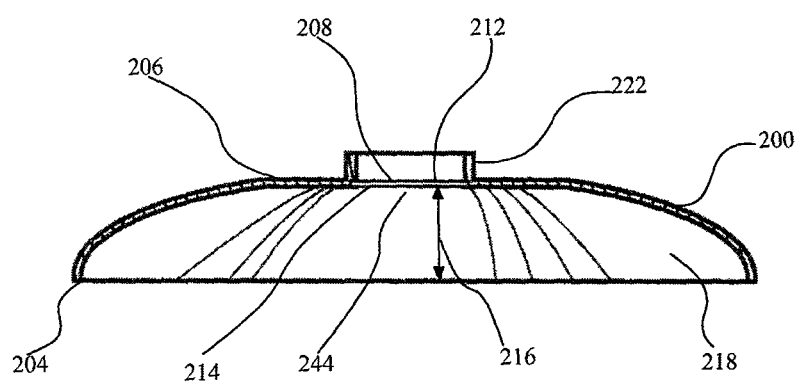
FIG. 10 is a side cross sectional view of the dome shaped cover.
Figure 11:
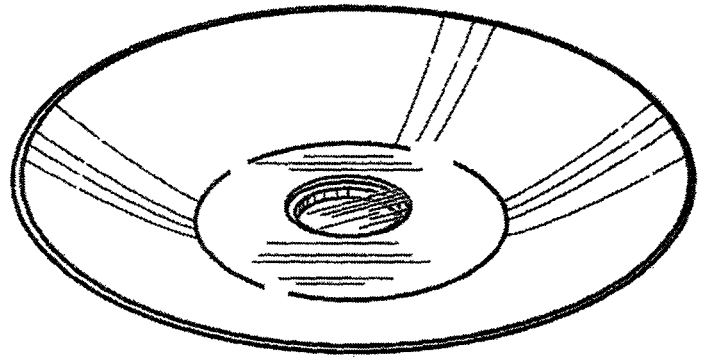
FIG. 11 is an perspective view of the bottom of the dome shaped cover.

Now also referring to FIG. 10, the geometry of the dome shaped cover is selected such that its cover volume 218 will substantially fully house the egg yolk 202 with some small amount of egg white 232 at the periphery 230 of the cover 203. The dimensions of cover 203 are selected such that a predetermined consistent yolk depth 216 and cover volume 218 are maintained. Yolk depth 216 measures from the horizontal surface 102 upward to the lower face 244 of transparent window 208.

Cover volume 218 of dome shaped cover 200 is approximately 30 ml was derived using the $95^{th}$ percentile confidence interval of a normal distribution of egg yolk volumes. The yolk depth 216 is approximately 9 mm, which by trial and error measurements were found to be the optimal yolk depth 216 to obtain consistent results. With the desired cover volume and yolk depth the diameter of the cover 203 results in an outer diameter of approximately 74 mm. In practice the cover volume 218, yolk depth 216 and the circumference can vary substantially and still provide adequate results, but via extensive trials it was found the geometry and dimensions proposed provide optimal, consistent and accurate results.

Method of Preparing the Egg and Deployment of Apparatus

Referring now to FIGS. 12 to 17 the method of preparing the egg and deployment of apparatus for determination of colour will be described.

Figure 12:
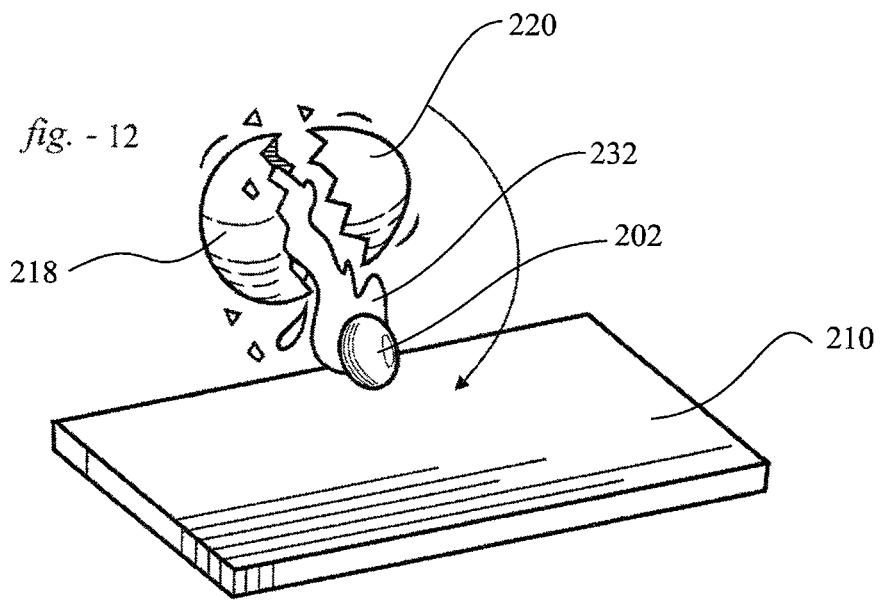
FIG. 12 depicts the first step in the method of preparing an egg: cracking the egg and placing its content on a flat opaque surface.

FIG. 12 depicts cracking an egg 220 and carefully separating the eggshell 218 from its inner contents, egg white 232 and egg yolk 202, and gently placing the contents on a horizontal flat surface 210 preserving the integrity of the egg yolk 202. It is vital that the egg yolk 202 is fully intact and does not rupture the vitelline membrane 250 in this process (breaking the yolk).

Figure 13:
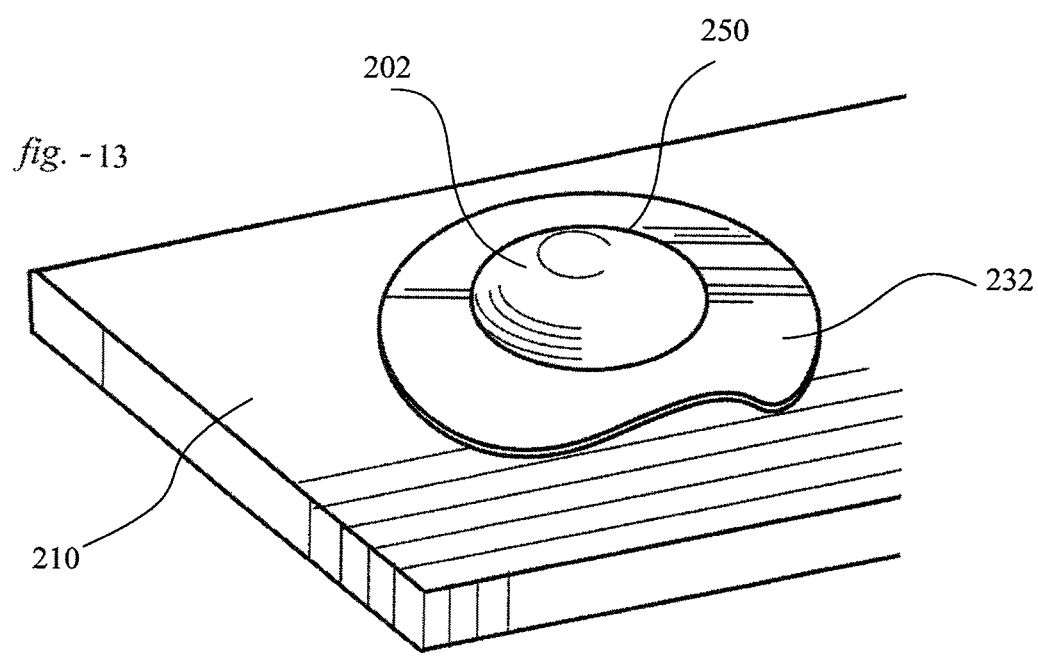
FIG. 13 depicts the method of preparing an egg: allowing the yolk to spread evenly over the flat surface.

FIG. 13 depicts a fully intact egg yolk 202 surrounded by the egg white 232 placed onto a horizontal flat surface 210 after a short rest period. The resting period allows gravity to settle the egg white 232 away from the top of the egg yolk 202, where the lower face 244 of transparent window 208 impinges onto the yolk top surface 220. This process allows for an unobstructed view to the yolk.

FIG. 14 depicts the recommended way of deploying the dome shaped cover 200 vertically downwards onto the egg yolk 202. This method is recommended as it affords a simultaneous overview of both the egg yolk and dome shaped cover 200 thus enabling the operator to gauge fit over the egg yolk 202. Placing the cover using other methods such as tilting the cover over the yolk may result in rupturing the vitelline membrane 250. The egg yolk 202 may rupture if caught between the horizontal flat surface 210 and base edge 204.

Observing via transparent window 208 a full and unobstructed contact between the yolk top surface 220 and the transparent window 208 can be ensured. Opaque ropes of egg white known as the chalaza anchor the yolk in the centre. The chalaza may get positioned between the transparent window 208 and the egg yolk 202, may lead to erroneous measurements.

FIG. 15 depicts that moving the dome shape cover 200 side to side as shown by arrow 271 in the event that the chalaza does obstruct the window, one can clear the window using this method. This provides a visual quality control ensuring that the egg yolk 202 positioned below the transparent window 208 is consistently free of unwanted obstructions such as the chalaza.

Figure 16:
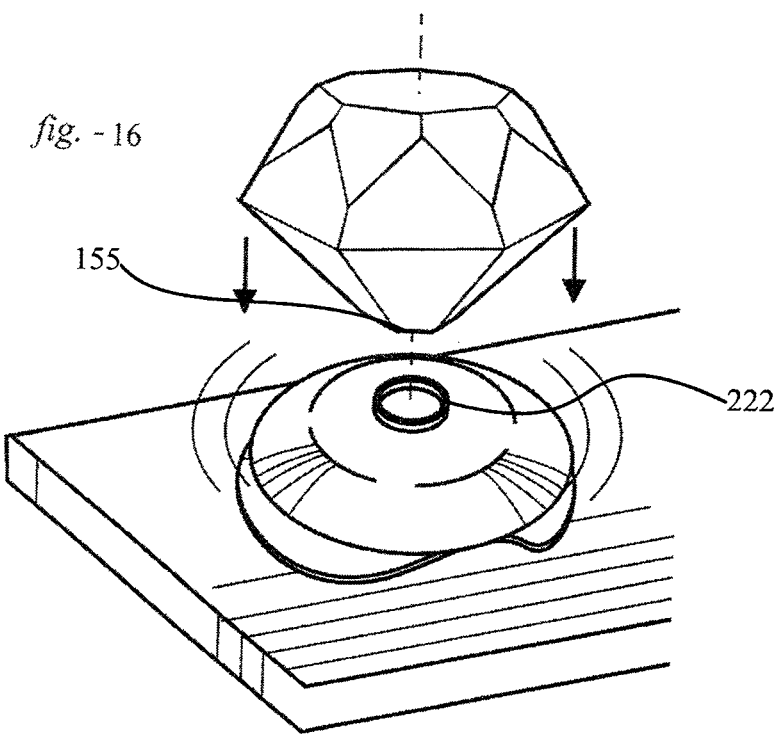
FIG. 16 depicts the procedure for attaching the colour sensor in FIG. 3 to the dome shaped cover once a proper and unobstructed contact with the yolk has been established.
Figure 17:
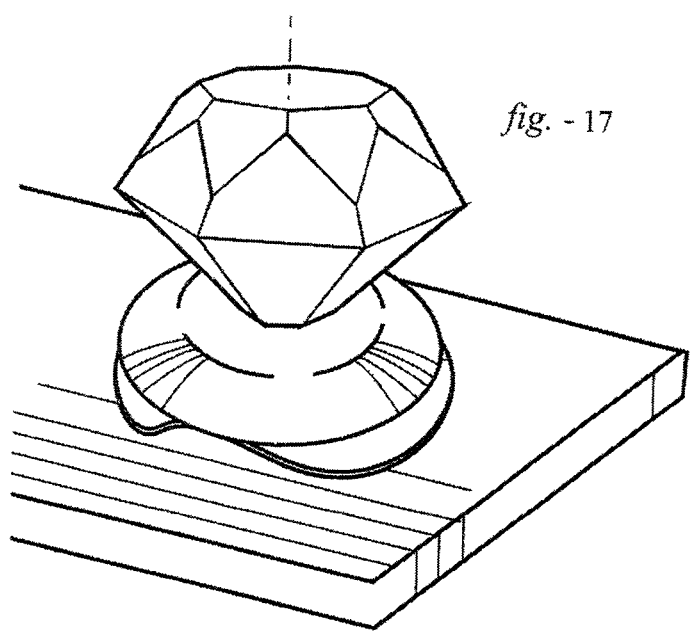
FIG. 17 illustrates a fully assembled apparatus with the colour sensor attached to the dome shaped cover deploying onto a yolk over a horizontal solid surface.

FIG. 16 depicts the recommended method of deploying the colour sensor 100 onto the cover 200. The mechanism by which the two components interlock involve the coupling of flange 222, best represented in FIG. 10, to the docking surface 155, best represented in FIG. 3. The method recommended to accomplish the coupling is by securely holding down the cover 203 with one hand and deploying the colour sensor 100 vertically downwards onto the cover. By attaching the colour sensor vertically downwards on to the widow 208 of the dome shape cover 200 minimizes the lateral movements that the cover would experience thus minimizing the disturbance experienced by the egg yolk 202. Minimizing any disturbance will reduce the possibility of egg yolk 202 to rupture and also retain the substantially unobstructed view obtained via methods described above.

At this point the colour measurement is taken and recorded as described for the portable colour sensor 100 above.

It should be apparent to persons skilled in the arts that various modifications and adaptation of this structure described above are possible without departure from the spirit of the invention the scope of which defined in the appended claim.

I claim:

1. An egg yolk cover for housing the liquid portion of an egg between the cover and a flat surface for the purpose of measuring egg yolk color, the egg yolk cover comprising:
   a) an opaque cover adapted to cover the liquid portion of an egg, the cover includes a base edge which contacts with the flat surface and adapted to create a substantially light tight seal with the flat surface;
   b) wherein the cover includes a transparent inspection area adapted for viewing the egg yolk.

2. The cover claimed in claim 1 wherein the cover is dome shaped and includes a flattened crown portion which is substantially parallel to the flat surface.

3. The cover claimed in claim 2 wherein the inspection area is an aperture in the flattened crown portion.

4. The cover claimed in claim 3 wherein the aperture includes a transparent window within the aperture which impinges onto the egg yolk.

5. The cover claimed in claim 4 wherein the cover defines a yolk depth wherein the flattened crown portion is dimensioned to be at a preselected height above the flat surface and selected to fall in the range from 6 to 12 mm inclusively.

6. The cover claimed in claim 5 wherein the cover defines a preselected volume between the cover and flat surface which is sufficient to house the egg yolk.

7. The cover claimed in claim 6 wherein the preselected volume is selected to fall in the range from 20 ml to 40 ml inclusively.

8. A method of determining the color of an egg yolk, the method comprising;
   a) cracking an egg onto a flat surface such that a liquid portion rests on the flat surface;
   b) placing a cover over the egg yolk the cover includes;
      i. an opaque cover adapted to cover the liquid portion of an egg, the cover includes with a base edge which contacts with the flat surface and adapted to create a substantially light tight seal with the flat surface;
      ii. wherein the cover includes a transparent inspection area adapted for viewing the egg yolk;
   c) deploying a color sensor onto the inspection area to measure the yolk color.

9. The method claimed in claim 8 wherein the cover is dome shaped and includes a flattened crown portion which is substantially parallel to the flat surface.

10. The egg yolk cover claimed in claim 9 wherein the inspection area is an aperture in the flattened crown portion.

11. The egg yolk cover claimed in claim 10 wherein the aperture includes a transparent window within the aperture which impinges onto the egg yolk.

12. The egg yolk cover claimed in claim 11 wherein the cover defines a yolk depth wherein the flattened crown portion is dimensioned to be at a preselected height above the flat surface and selected to fall in the range from 6 to 12 mm inclusively.

13. The egg yolk cover claimed in claim 12 wherein the cover defines a preselected volume between the cover and flat surface which is sufficient to house the egg yolk.

14. The egg yolk cover claimed in claim 13 wherein the preselected volume is selected to fall in the range from 20 ml to 40 ml inclusively.

15. The method claimed in claim 8 wherein the light sensor is a portable colour sensor for measuring colour of a substrate comprises:
   a) a single flat printed circuit board with a top & bottom side which includes at least one LED light and one colour sensor;
   b) at least one light pipe receiving light from the LED and transmitting it onto a substrate at an angle theta;
   c) a tube frame including an optical tube for receiving light reflections from the substrate; and
   d) wherein the light pipes and the tube frame, are compression fit between the printed circuit board and a lower housing.

16. The method claimed in claim 15 wherein the LED light is directed perpendicularly away from the printed circuit board and wherein the light pipe is an arcuate member bending the light to achieve the angle theta.

17. The method claimed in claim 15 wherein the light pipe abutting at one end to the LED and connecting at the other end at a light emitting port in the lower housing.

18. The method claimed in claim 17 wherein the light emitting port is located within a light cavity which is an inverted dome with the bottom terminating at a contact surface.

19. The method claimed in claim 18 wherein the flattened crown portion contacting with the contact surface of the lower housing of the lower housing of the colour sensor.

* * * * *